United States Patent
Dysarz

[11] Patent Number: 6,016,595
[45] Date of Patent: Jan. 25, 2000

[54] METHOD AND DEVICE TO FORM A SPRING NEEDLE CANNULA

[76] Inventor: Edward D. Dysarz, 11423 Triola La., Houston, Tex. 77072

[21] Appl. No.: 09/185,565

[22] Filed: Nov. 4, 1998

[51] Int. Cl.[7] .................................................... B23P 17/00
[52] U.S. Cl. ........................... 29/423; 29/896.9; 604/272; 604/274
[58] Field of Search .................................. 29/423, 896.9; 72/135, 146, 370.01, 466.2; 604/272, 273, 274, 195

[56] References Cited

U.S. PATENT DOCUMENTS

| | | |
|---|---|---|
| 214,874 | 4/1879 | Beugnies . |
| 458,115 | 8/1891 | Thomson . |
| 1,568,369 | 1/1926 | Everett . |
| 1,827,766 | 10/1931 | Rosenburgh . |
| 2,329,286 | 9/1943 | Meyer . |
| 2,516,930 | 8/1950 | Varian . |
| 2,717,600 | 9/1955 | Huber . |
| 2,841,866 | 7/1958 | Schilling . |
| 2,850,014 | 9/1958 | Ginsburg . |
| 3,010,197 | 11/1961 | Roehr . |
| 3,174,517 | 3/1965 | Wilson . |
| 3,251,126 | 5/1966 | Himstedt . |
| 3,362,061 | 1/1968 | Krasnitz . |
| 3,755,872 | 9/1973 | Dorsey . |
| 4,963,306 | 10/1990 | Weldon . |
| 4,968,302 | 11/1990 | Schluter et al. . |
| 5,018,530 | 5/1991 | Rank et al. . |
| 5,084,024 | 1/1992 | Skinner . |
| 5,353,800 | 10/1994 | Polndorf et al. . |
| 5,405,376 | 4/1995 | Mulier et al. . |

FOREIGN PATENT DOCUMENTS

| | | | |
|---|---|---|---|
| 520103 | 7/1976 | U.S.S.R. | ................................. 604/272 |
| 621283 | 4/1949 | United Kingdom | .................... 604/274 |

*Primary Examiner*—David P. Bryant
*Assistant Examiner*—John Preta

[57] ABSTRACT

A needle cannula with a first end and a second end wherein a section near said second end must be shaped into a coiled spring and then pulled into a biased spring needle cannula without destorting the inside surface of said spring needle cannula. A wire of suitable section is inserted into said cannula of said spring needle cannula and wherein said first end of said spring needle cannula is inserted into a hole formed in a retainer plate and wherein a portion of said spring needle cannula with said wire in said cannula is wrapped or coiled about a coil bar wherein said needle cannula is formed into a spring needle cannula and wherein the inside walls of said cannula cannot deform due to said wire disposed in said cannula. The coiled spring needle cannula with said wire inside is removed from said coil bar and further installed into a modullar hub chamber and further stretched to a suitable length wherein said stretched spring needle cannula becomes a biased spring needle cannula wherein said biased spring needle cannula is inserted into a hub chamber and wherein said biased spring needle cannula is suitably fixed to said hub chamber wherein said first end of said biased spring needle cannula extends forward froming a straight needle cannula and wherein said wire is removed from said biased spring needle cannula.

5 Claims, 4 Drawing Sheets

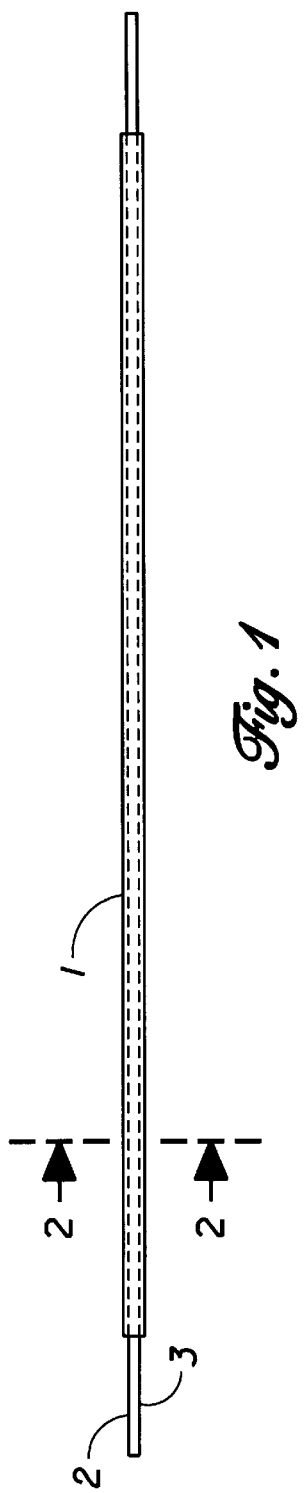
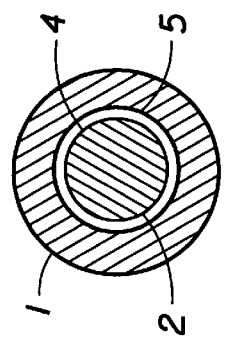
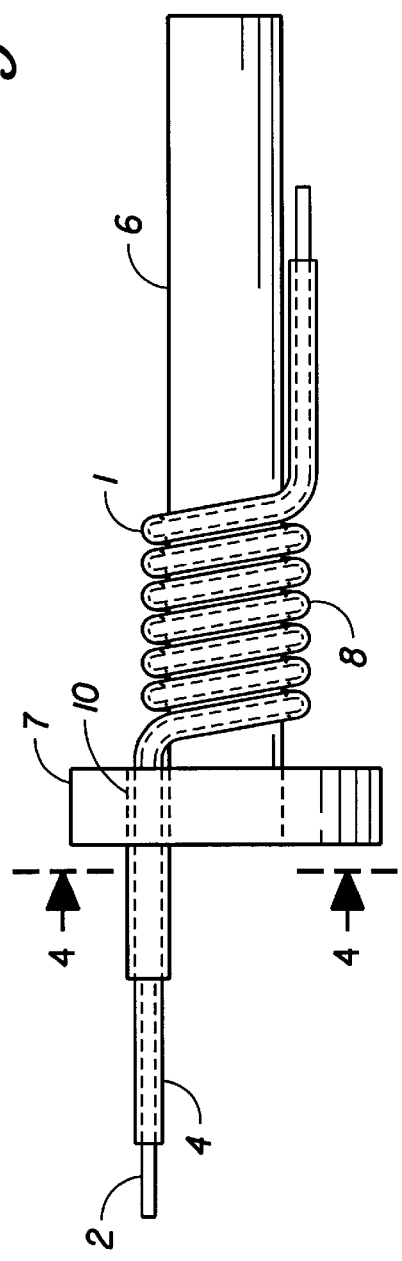

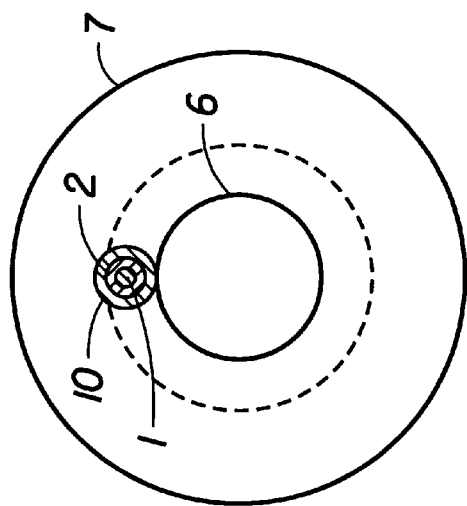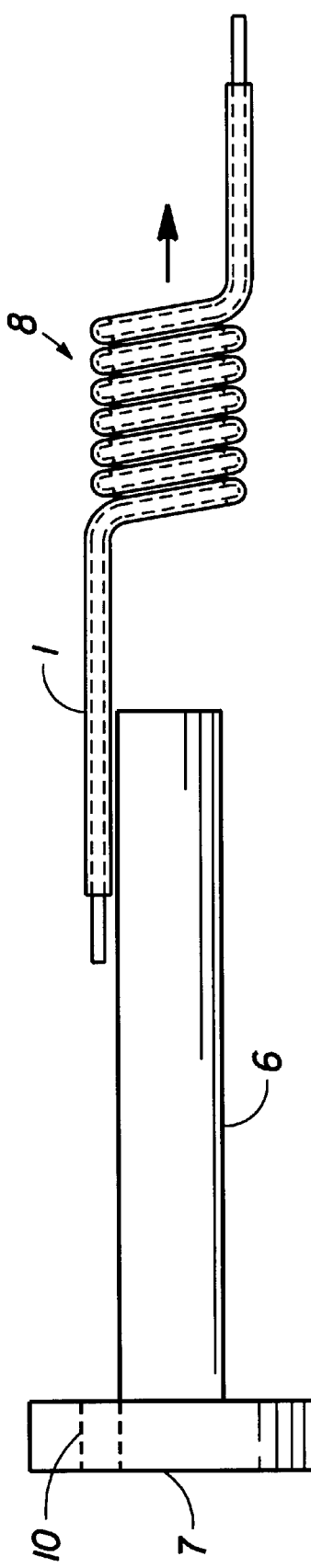

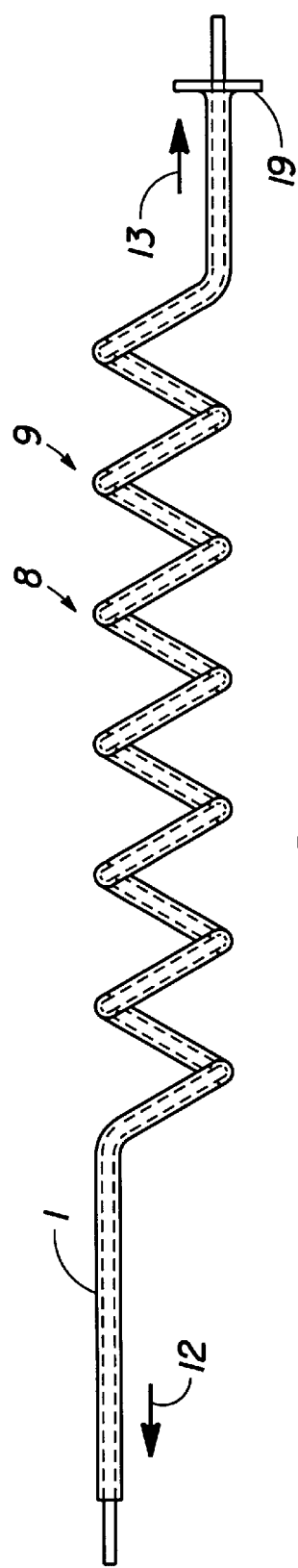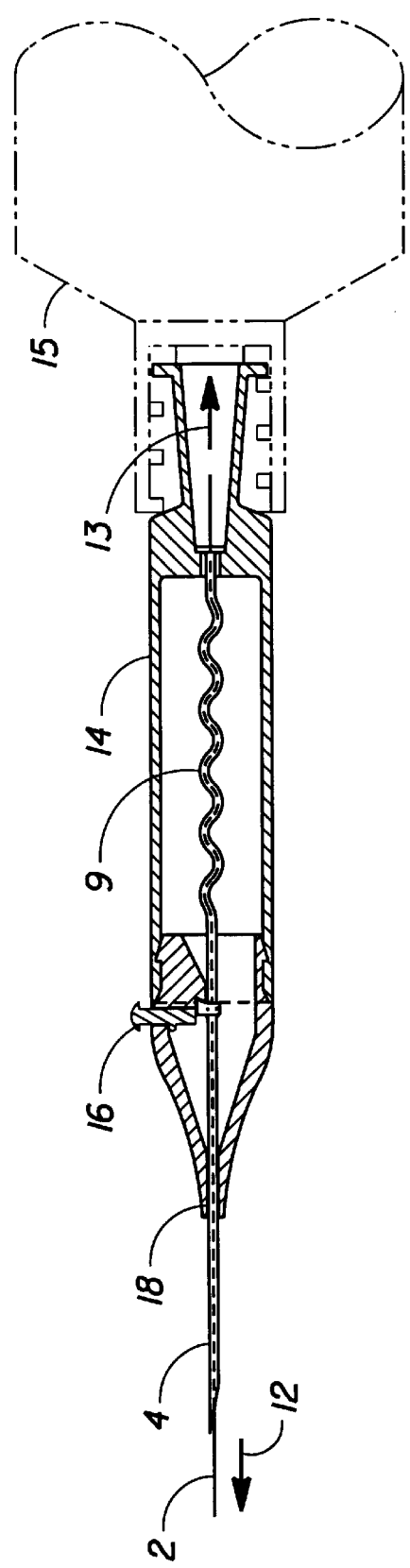

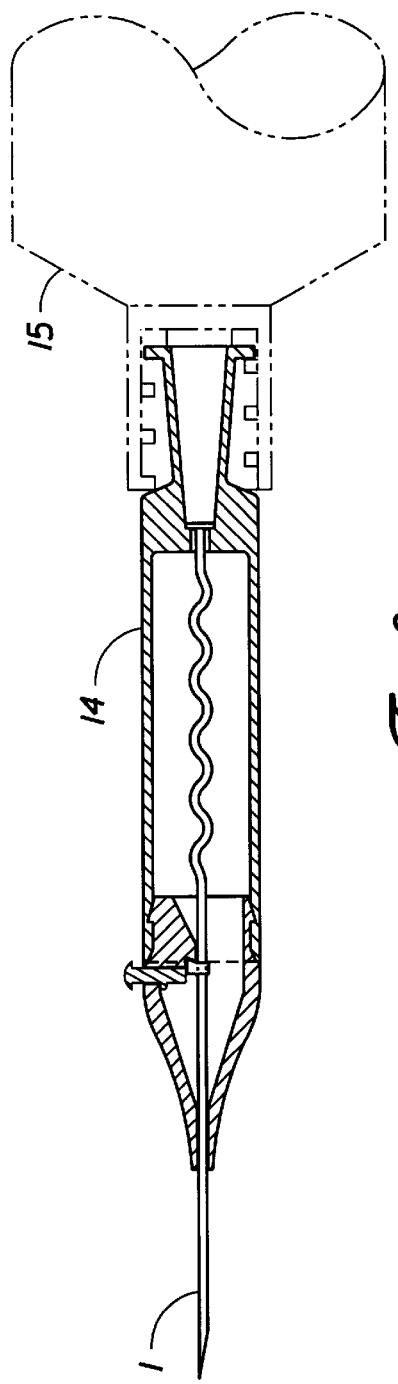
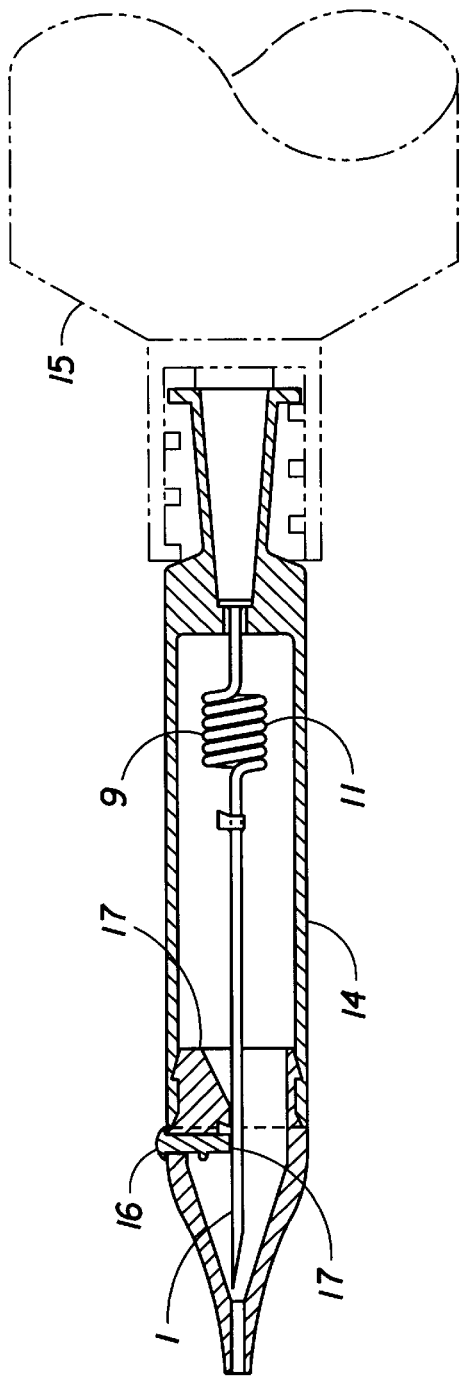

METHOD AND DEVICE TO FORM A SPRING NEEDLE CANNULA

BACKGROUND OF THE INVENTION

There are many types of safety syringes, blood sampling devices, and IV cathaters patented, however none of these devices teach a coiled or biased spring needle cannula therefore a purpose of developing a method and a device to form a spring needle cannula does not exist.

SUMMARY

It is the object of this invention to provide a means to manufacture a biased spring needle cannula without collapsing or destroying the cannula walls.

The foregoing and other objects and advantages are attained by a wire with a proper diameter inserted into the cannula of a needle cannula, coiling said needle cannula about a shaft, forming a spring needle cannula and further stretching said spring needle cannula into a biased spring needle cannula and further suitably installing said biased spring needle cannula into a hub chamber forming a biased spring needle cannula contained in a module and fixed to a syringe.

The features of the present invention can be best understood with further objects and advantages by referrence to the following descriptions taken in conjunction with accompanying drawings wherein like numerals indicate like parts.

BRIEF DESCRIPTIONS OF THE DRAWINGS

FIG. 1 is an elevation view of a needle cannula with a wire inserted into said cannula.

FIG. 2 is a section elevation as taken through FIG. 1.

FIG. 3 is an elevation view of a needle cannula being coiled about a shaft.

FIG. 4 is a section elevation as taken through FIG. 2.

FIG. 5 is an elevation view of the spring needle cannula being removed from the shaft.

FIG. 6 is an elevation view of the spring needle cannula with a wire in the cannula.

FIG. 7 is a section elevation view of a biased spring needle cannula in a module with a wire in cannula.

FIG. 8 is a section elevation view of a biased spring needle cannula in a module with the wire withdrawn.

FIG. 9 is a section elevation of the first end of the spring needle cannula in the elongated hollow tube.

DETAILED DESCRIPTION OF THE PREFERRED EMBODIMENT

Referring to FIG. 1 there is shown an elevation view of a needle cannula 1 with an anti deformation wire 2 inserted into the needle cannula 1.

The needle cannula 1 has a first end, a cenral section and a second end, a cannula, an inside surface and an outside surface. The anti deformation wire has a first end, a second end and an outside surface. A lubricant 3 or a low friction cladding is placed on the outside of the anti deformation wire 2 to faiclitate the insertion or removal of the anti deformation wire 2 from the cannula of the needle cannula 1.

A sufficient section of anti deformation wire 2 is shown extending from the first end and the second end of the needle cannula 1 wherein the anti deformation wire 2 may be grasped with suitable tools or machinery to either insert the anti deformation wire 2 into the cannula of the needle cannula 1 or to grasp the anti deformation wire 2 and to pull it out of the needle cannula 1.

Referring to FIG. 2 there is shown a section view of the needle cannula 1 and the anti deformation wire 2 inside of the cannula 4. An annulus 5 is shown between the inside surface of the needle cannula 1 and the exterior surface of the anti deformation wire 2; this is a area that a lubricant or cladding would be applied. The annulus 5 also provides a suficient space to install the anti deformation wire into the cannula 4 or remove the anti deformation wire 2 from the cannula 4.

Referring to FIG. 3 there is shown a section elevation view of a coil bar 6 with a stop plate 7.

The coil bar 6 is shown with a first end and a second end wherein the first end of the coil bar 6 is suitably fixed to the second side of the stop plate 7. The stop plate 7 is shown with a hold hole 10 that is formed in said stop plate wherein the hold hole 10 extends from the first side to the second side of said stop plate 7.

The first end of the needle cannula 1 with the anti deformation wire 2 inside of the needle cannula 1 is inserted into the hold hole 10 formed in the stop plate 7. The center section of the needle cannula 1 with the anti deformation wire 2 is wound around the coil bar 6 into a tight coil 11 wherein the needle cannula is formed into a spring needle cannula 8. If necessary, heat may be applied to the needle cannula to further form the needle cannula 1 into a spring needle cannula 8. If necessary the needle cannula may be peened or tapped to further form the needle cannula into a spring needle cannula 8.

Referring to FIG. 4 there is shown a section elevation view of the needle cannula 1 and the stop plate 7.

The first end of the needle cannula 1 is shown with the anti deformation wire 2 extending from the needle cannula. The first end of the needle cannula is held in the hold hole 10 to suitably hold the needle cannula 1 and the anti deformation wire 2 while the needle cannula 1 is being coiled around the coil bar 6.

Referring to FIG. 5 there is shown an elevation view of the needle cannula 1 or what is now the spring needle cannula 8 being removed from the coil bar 6.

The second end of the spring needle cannula 8 is pulled off the coil bar 6 and the first end of the spring needle cannula 8 is pulled out of the hold hole 10 formed in the stop plate 7.

Referring to FIG. 6 there is shown an elevation view of the spring needle cannula 8 being stretched into a biased spring needle cannula 9.

The first end is shown being pulled in the first direction 12 and the second end is shown being pulled in the second direction 13 thereby putting bias into the spring needle cannula 1 thereby forming a bias spring needle cannnula 9.

The anti deformation wire 2 is still in the bias needle cannula at this time. A flange 19 is shown suitably fixed to the second end of the needle cannula 1.

Referring to FIG. 7 there is shown a biased spring needle cannula 9 suitably fixed to the inside of a hub module 14 that is fixed to the first end of a syringe 15. The hub module 7 has a latch means 16 and a guide tunnel 18.

The biased spring needle cannula 9 still has the anti deformation wire 2 disposed in the cannula 4. The anti deformation wire 2 is shown extending from the first end to the biased spring needle cannula 9 and the anti deformation wire 2 is shown extending from the second end of the biased spring needle cannula 9.

Referring to FIG. 8 there is shown a section elevation view of the biased spring needle cannula 1 in the hub module 14.

The anti deformation wire has been removed and the biased spring needle cannula 9 is ready to be used as a conduit to transport medicament from the syringe 15 into a body.

Referring to FIG. 9 there is shown a section elevation of the hub module 14 with the spring needle cannula 1 suitably contained in the hub module 14.

The biased spring needle cannula has been used to inject medicament into the body and the latch release means 17 has been activated to release the biased spring needle cannula 9. The biased spring needle cannula 9 has pulled itself entirely into the hub module 14 where the coils 11 reforms between the first end and the second end of the spring needle cannula 8. The point of the first end of the spring needle cannula has been completly enclosed in the hub module 14 and therefore cannot accidentaly prick or otherwise injure another person.

Although the system described in detail supra has been found to be most satisfactory and preferred, many variations are possible. For example the anti deformation wire could be looped on the first end and the second end to enable machines to grasp the anti deformation wire, the cannula could also be pressurized to prevent any distortions.

Although the invention has been described with reference to the preferred embodiment, it will be understood by those skilled in the art, that additions, modifacations, substitutions, deletions and other details herein are to be interpreted as illustrative and are not in a limiting sense.

What is claimed as invention is:

1. A method of making a retractable needle syringe having a biased spring needle cannula, the method comprising;

providing a hollow needle cannula with a first end and a second end, providing an anti deformation wire with a first end and a second end, providing a coil bar with a first end and a second end having a stop plate affixed thereto, wherein the stop plate has a first side, a second side affixed to the coil bar, and a hold hole, forming a wire containing needle cannula by inserting the anti deformation wire into the first end of the needle cannula until it is substantially flush with or protrudes past the second end of the needle cannula, inserting one end of the wire containing needle cannula into the hold hole of the stop plate, winding the other end of the wire containing needle cannula around the coil bar to form the spring needle cannula, leaving some portion of the other end of the wire containing needle cannula in a straightened state, such that the anti deformation wire prevents the needle cannula from collapsing during the winding step, removing the wire containing needle cannula from the coil bar, stretching the wire containing needle cannula so as to form a biased spring needle cannula, removing the anti deformation wire, and assembling the spring needle cannula into a syringe module so as to form a retractable spring needle cannula syringe.

2. The method of claim 1 wherein an annulus is formed between said anti deformation wire and said cannulas.

3. The method of claim 1 wherein said anti deformation wire is clad with a low friction material.

4. The method of claim 2 wherein a lubricant is inserted into said annulus formed between said anti deformation wire and said annulus.

5. The method of claim 1 wherein a flange is fixed to said second end of said needle cannula.

\* \* \* \* \*